US012406396B2

(12) United States Patent
Stopp et al.

(10) Patent No.: US 12,406,396 B2
(45) Date of Patent: Sep. 2, 2025

(54) MICROSCOPE CAMERA CALIBRATION

(71) Applicant: Brainlab AG, Munich (DE)

(72) Inventors: Sebastian Stopp, Munich (DE); Johannes Manus, Munich (DE)

(73) Assignee: Brainlab AG, Munich (DE)

( * ) Notice: Subject to any disclaimer, the term of this patent is extended or adjusted under 35 U.S.C. 154(b) by 282 days.

(21) Appl. No.: 18/009,436

(22) PCT Filed: Aug. 10, 2020

(86) PCT No.: PCT/EP2020/072391
§ 371 (c)(1),
(2) Date: Dec. 9, 2022

(87) PCT Pub. No.: WO2022/033656
PCT Pub. Date: Feb. 17, 2022

(65) Prior Publication Data
US 2023/0260158 A1 Aug. 17, 2023

(51) Int. Cl.
G06K 9/00 (2022.01)
A61B 90/20 (2016.01)
(Continued)

(52) U.S. Cl.
CPC ............... G06T 7/85 (2017.01); A61B 90/20 (2016.02); A61B 2034/2065 (2016.02); G06T 2207/10056 (2013.01)

(58) Field of Classification Search
CPC ... G06T 7/85; G06T 2207/10056; G06T 7/73; G06T 7/80; A61B 90/20;
(Continued)

(56) References Cited

U.S. PATENT DOCUMENTS 5,086,401 A * 2/1992 Glassman ................. A61F 2/46
606/88
5,513,005 A * 4/1996 Muller .................... A61B 90/20
250/201.3
(Continued)

FOREIGN PATENT DOCUMENTS

AU 2024219905 A1 * 10/2024 ............. A61B 34/30
CN 110403699 A * 11/2019 ......... A61B 17/2256
(Continued)

OTHER PUBLICATIONS

Garcia, et al.; Calbration of a surgical microscope with automated zoom lenses using an active optical tracker, Feb. 14, 2008, 8 pages.
(Continued)

Primary Examiner — Shervin K Nakhjavan
(74) Attorney, Agent, or Firm — Tucker Ellis LLP

(57) ABSTRACT

The present disclosure relates to a computer-implemented method for calibrating an optical system of a surgical microscope, a corresponding computer program, a computer-readable storage medium storing such a program and a computer executing the program, as well as a medical system comprising an electronic data storage device and the aforementioned computer. The present disclosure further relates to a computer-implemented method, a computer program and a system for determining the spatial position of an object to be tracked not only via the surgical microscope, but also via a separate detection system. In case a deviation between the detected spatial positions is recognized, the optical system of the surgical microscope is re-calibrated.

20 Claims, 3 Drawing Sheets

(51) Int. Cl.
*G06T 7/80* (2017.01)
*A61B 34/20* (2016.01)

(58) Field of Classification Search
CPC ............ A61B 2034/2065; A61B 34/20; A61B 2034/2055; A61B 2034/2068; A61B 2090/0818
See application file for complete search history.

(56) References Cited

U.S. PATENT DOCUMENTS

| | | | | |
|---|---|---|---|---|
| 5,999,837 | A * | 12/1999 | Messner | ............ G02B 21/0012 600/407 |
| 6,351,661 | B1 * | 2/2002 | Cosman | .................... G06T 3/14 600/417 |
| 9,188,973 | B2 * | 11/2015 | Tenney | .................. H04N 7/181 |
| 9,572,539 | B2 * | 2/2017 | Carrat | ...................... A61B 6/12 |
| 10,130,430 | B2 * | 11/2018 | Kao | ....................... A61B 90/98 |
| 10,846,883 | B2 * | 11/2020 | Urban | ........................ G06T 7/20 |
| 11,295,484 | B2 * | 4/2022 | Scherer | ...................... G06T 7/90 |
| 11,357,574 | B2 * | 6/2022 | Krüger | ................... A61B 90/98 |
| 11,592,655 | B2 * | 2/2023 | Ko | ............................ G06T 5/90 |
| 11,744,653 | B2 * | 9/2023 | Themelis | ................ G06F 3/017 600/429 |
| 12,068,074 | B2 * | 8/2024 | Hu | ......................... G16H 30/20 |
| 2022/0401178 | A1 * | 12/2022 | Polchin | .................. A61B 34/20 |

FOREIGN PATENT DOCUMENTS

| | | | | |
|---|---|---|---|---|
| CN | | 111491151 A * | 8/2020 | ............ A61B 34/20 |
| WO | WO-2016066287 A1 * | | 5/2016 | ............. A61B 34/20 |

OTHER PUBLICATIONS

Drouin, et al.; IBIS: an OR ready open-source platform for image-guided neurosurgery, Aug. 31, 2016, 16 pages.

* cited by examiner

MICROSCOPE CAMERA CALIBRATION

RELATED APPLICATION DATA

This application is a National Phase application of International Application No. PCT/EP2020/072391, filed Aug. 10, 2020, the contents of which are incorporated herein by reference.

FIELD OF THE INVENTION

The present invention relates to a computer-implemented method for calibrating an optical system of a surgical microscope, a corresponding computer program, a computer-readable storage medium storing such a program and a computer executing the program, as well as a medical system comprising an electronic data storage device and the aforementioned computer.

TECHNICAL BACKGROUND

Modern microscopes used within an O.R. are often spatially tracked with respect to a patient, which not only allows a visualisation of the microscope's optical axis and focal point with respect to the patient's anatomy on a dedicated monitor or display, but also allows to implement augmented reality, i.e. provide a semi-transparent visualisation of for example surgical targets as an overlay over the view on the patient as seen through the microscope.

In recent years, procedures for spatially tracking objects, i.e. for determining the spatial position (including the spatial location and/or the spatial orientation) of one or more objects is often based on optical images of those objects, which are obtained via one or more cameras. Provided that the spatial position of these cameras is known and the relative position between the objects to be tracked and the camera can be derived from the images obtained from the camera with sufficient accuracy, the object's spatial position can not only be calculated with respect to the camera, but also with respect to any other object or coordinate system with a known relative position to the camera.

WO 2006/095027 discloses an approach for calculating intrinsic and extrinsic parameters for calibrating an optical microscope as a function of the microscope's magnification and focus.

WO 2017/157763 discloses an approach of simultaneously tracking an instrument based on images received from a surgical microscope on the one hand, and based on images received from an optical tracking system on the other hand.

Adjustable zoom- and/or focus-settings of surgical microscopes however affect tracking based on images obtained via a surgical microscope. This is because the optical path within the microscope and therefore also the position to which the image of objects is projected to within the microscope may change with every adjustment made on the focus and/or the zoom. As a consequence thereof, high demands on accuracy as placed by spatial tracking regularly cannot be fulfilled by such microscopes.

The present invention has the object of improving accuracy of microscope-based optical tracking, thereby even providing an approach that allows to base optical tracking on images obtained from a surgical microscope having adjustable zoom- and/or focus-settings.

The present invention can be used in connection with microscope navigation, i.e. procedures which involve the use of a surgical microscope the spatial position of which is tracked with respect to a patient a surgical procedure is to be carried out on, particularly wherein the microscope is utilised to track objects within the microscope's optical field of view.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses determining the spatial position of an object to be tracked not only via the surgical microscope, but also via a separate detection system. In case a deviation between the detected spatial positions is recognised, the optical system of the surgical microscope is re-calibrated.

GENERAL DESCRIPTION OF THE INVENTION

In this section, a description of the general features of the present invention is given for example by referring to possible embodiments of the invention.

The computer-implemented medical method according to the present invention for calibrating an optical system of a surgical microscope comprises the following steps:
a) first position data is acquired via the optical system having a first calibration, which describes a spatial position of an object within a first co-ordinate system assigned to the optical system;
b) second position data is acquired via a detection system being separate from the optical system, which describes a spatial position of the object within a second co-ordinate system assigned to the detection system;
c) transformation data is acquired which describes a co-ordinate transformation between the first co-ordinate system and the second co-ordinate system;
d) calibration data is determined based on the first position data, the second position data and the transformation data, which describes a second calibration of the optical system, for which the object's spatial position acquired via the optical system aligns with the object's spatial position acquired via the detection system;
e) adjusted first position data is acquired via the optical system having the second calibration, which describes the spatial position of the object within the first co-ordinate system assigned to the optical system.

In a (for example first) exemplary step, the spatial position of the object to be tracked, for example a medical instrument such as a pointer instrument is tracked by using the surgical microscope. The surgical microscope comprises an optical system which guides an optical path of an image received by the optical system towards an optical receiver such as a CCD-sensor which transmits data describing the received image. Optionally, the optical path may also be guided to one or more eyepieces of the microscope which allow a surgeon to directly observe the received image. Based on the data transmitted by the optical receiver, the spatial position of the tracked object is determined within a co-ordinate system assigned to the optical system and/or to the microscope.

In a (for example second) exemplary step and in a similar manner, the spatial position of the object is simultaneously determined by a detection system that does not form part of the microscope's optical system, but rather represents an entity separate from the surgical microscope. Based on the data received therefrom, the object's spatial position is then determined within a co-ordinate system assigned to the detection system and/or an optical system thereof.

For correlating the object's spatial position determined within these two separate co-ordinate systems, a spatial transformation between the co-ordinate systems needs to be defined in a (for example third) exemplary step. This transformation may be predefined but may also be defined by performing any applicable calibration procedure known in the art. Basically, such transformation allows to describe any spatial position determined within one co-ordinate system within the respective other co-ordinate system.

Based on the data acquired so far, the object's spatial position as detected by the detection system can be compared with the object's spatial position as detected by the microscope in a (for example fourth) exemplary step. Assuming that the detection system correctly indicates the object's spatial position, a deviation of the position detected by the microscope would indicate that the microscope's calibration is incorrect. In such case measures can be taken to correct the microscope's calibration such that it correctly detects the object's spatial position in alignment with the detection system.

In a (for example fifth) exemplary step the object's spatial position is determined via the re-calibrated microscope.

In a first example of the method, the first calibration and/or the second calibration of the optical system includes at least one of:
  an intrinsic calibration of a monoscopic or a stereoscopic camera of the surgical microscope;
  an extrinsic calibration of a monoscopic or a stereoscopic camera of the surgical microscope with respect to a monoscopic or a stereoscopic camera of the detection system;
and/or
wherein the second calibration partially reflects the first calibration.

With the present approach the microscope can be re-calibrated intrinsically and/or extrinsically. As used herein, an intrinsic calibration relates to an "inner" calibration of a camera(-system) of the microscope. This may include a calibration of two monoscopic cameras forming a stereoscopic camera. On the other hand, an extrinsic calibration relates to a calibration of cameras which are assigned to different systems, i.e. the detection system on the one hand and the microscope on the other hand.

In this regard, it is important to note that the present invention does not require a "full" re-calibration of the one or more microscope cameras. Rather, the previous (first) calibration may be partially maintained, wherein the remaining parts are replaced by more accurate parts of the second calibration.

If, in a specific example, specific parts of the microscope calibration (for example a calibration within certain spatial directions) are expected to remain unaffected by certain manipulations of the surgical microscope (for example adjusting the zoom or the focus) these parts of the first calibration may remain unamended, with the other parts of the first calibration being replaced by the respective parts of the second calibration.

In a further example, acquiring first position data involves detecting a first, particularly a distal section of the object and/or acquiring second position data involves detecting a second, particularly a proximal section of the object. Determining calibration data may be based on object model data which describes a predefined relative position between the first section and the second section.

In a specific example, the microscope camera may be used to track a distal portion of a medical instrument, wherein the camera of the detection system tracks a proximal portion of the same instrument, which does not even need to be located within the field of view of the microscope camera.

In such cases, it is necessary to know the invariant spatial relationship between the detected portions of the instrument such that it can be determined whether or not a spatial position as detected by the microscope deviates from a spatial position as detected by the detection system.

In a further example, detecting the object may involve detecting tracking markers attached to the object, wherein the microscope camera may detect tracking markers which are different to the markers detected by the detection system. In particular, a first or distal portion of the object may be provided with so-called "ring-markers", i.e. optically detectable rings in a specific arrangement and/or of a specific width which run around a cylindrical part of the instrument.

Further, the proximal section of the object may be provided with conventional tracking markers such as retro-reflective marker spheres or one or more 2D-markers showing a specific, optically detectable pattern.

In a further specific example, the first position data is determined from one or more images received from a monoscopic or a stereoscopic camera of the surgical microscope, particularly an integrated microscope camera. Further, the camera of the surgical microscope may have a variable zoom-setting and/or a variable focus-setting.

In a similar manner, the second position data may be determined from one or more images received from a monoscopic or a stereoscopic camera of the detection system, particularly wherein the camera of the detection system is rigidly coupled to the surgical microscope and/or is provided as a component separate to the surgical microscope. Further, the camera assigned to the detection system may have a larger field of view than the microscope camera and/or wherein the camera of the detection system has a visual axis that is angled with respect to the visual axis of the microscope camera.

In a further specific example, the detection system, particularly the camera of the detection system has a predefined zoom-setting and/or a predefined focus-setting.

In a further specific example, the method as described herein is performed
  upon user request;
  before the surgical microscope is operated;
  in predefined time intervals during the operation of the surgical microscope;
  after the setting of the surgical microscope has been changed, particularly after the viewing direction of the surgical microscope and/or the viewing distance of the surgical microscope has changed; and/or
  after the setup of the optical system, particularly the zoom-setting of the optical system and/or the focus-setting of the optical system has changed.

While it is conceivable that the microscope camera is re-calibrated only in certain cases which are expected to result in an incorrect microscope calibration, it is also conceivable to perform the method as described herein on a regular basis, for example constantly and as long as the microscope camera is used for tracking purposes, or at predefined time intervals, for example every few seconds or minutes.

Moreover, the microscope camera may be re-calibrated only if its detection misalignment with respect to the detection system increases a predefined threshold. In particular, the present approach may include the step of:

determining deviation data based on the first position data, the second position data and the transformation data, describing a spatial deviation between the object's spatial position acquired via the optical system and the object's spatial position acquired via the detection system, wherein calibration data is determined if the spatial deviation exceeds a predefined threshold.

As long as the object/instrument is located within the field of view of the respective cameras, its spatial position may be simultaneously tracked on the basis of the adjusted first position data and the second position data. In particular, the spatial position within at least one degree of freedom is determined based on a weighted combination of the adjusted first position data and the second position data.

In a further example, detecting the object may involve detecting tracking markers attached to the object, wherein the microscope camera may detect tracking markers which are different to the markers detected by the detection system. In particular, a first or distal portion of the object may be provided with so-called "ring-markers", i.e. optically detectable rings in a specific arrangement and/or of a specific width which run around a cylindrical part of the instrument.

Further, the proximal section of the object may be provided with conventional tracking markers such as retro-reflective marker spheres or one or more 2D-markers showing a specific, optically detectable pattern. In a specific example, a first camera(-system) detects a 6D Pose $X_i$; i=1 . . . 6 from n measurements $a_j$; j=1 . . . n that may for example indicate feature-points of an image of the object itself or a marker attached thereto. These measurements are linked to each other depending on the pose $$a_j = a_j(X_i)$$

which allows to define the function $$F(X_i, a_{m,j}) = \sum_j (a_j(X_i) - a_{m,j})^2$$

This function can be solved with a minimisation technique and an appropriate initial value for the pose:

$$\delta F(X_i, a_{m,j}) = 0 \Rightarrow X_i$$

A usual problem to be solved is that the measurements and therefore the above function may show a strong reaction to some alterations of the pose, whereas other alterations of the pose only cause a weak response:

$$\left[\frac{\partial F(X_i, a_{m,j})}{\partial X_l}\right] \gg \left[\frac{\partial F(X_i, a_{m,j})}{\partial X_k}\right]; l \in S_1; k \in S_2$$

wherein $S_1$ and $S_2$ are disjunct sub-quantities of the six degrees of freedom.

In a similar manner, the second camera (-system) determines the 6D position $Y_i$; i=1 . . . 6 of the object or marker thereto from m measurements $b_j$; j=1 . . . m:

$$b_j = b_j(Y_i).$$

With the known transformation between the co-ordinate systems assigned to the respective cameras, the pose $Y_1$ can be transformed to the pose $\tilde{X}_t$ within the co-ordinate system of the first camera. Thus, the pose can also be determined based on the second set of measurements:

$$G(\tilde{X}_t, b_{m,j}) = \sum_j (\tilde{b}_j(\tilde{X}_t) - b_{m,j})^2$$

$$\delta G(\tilde{X}_t, b_{m,j}) = 0 \Rightarrow \tilde{X}_t.$$

A straightforward approach in order to improve pose detection would include determining an average value from both detected poses.

A further approach disclosed herein is based on the following assumption:

$$\left[\frac{\partial G(X_i, a_{m,j})}{\partial X_l}\right] \gg \left[\frac{\partial G(X_i, a_{m,j})}{\partial X_k}\right]; l \in \tilde{S}_1; k \in \tilde{S}_2$$

with $S_1 \cap \tilde{S}_1 \sim 0$, i.e. $\tilde{S}_1 = S_2$. This means that both systems are complementary with respect to the degrees of freedom, which allows to determine an improved combination by the following function:

$$\delta[w_F \cdot F(X_i, a_{m,j}) + w_G \cdot G(X_i, b_{m,j})] = 0 \Rightarrow X_i$$

For different directions, only one function reacts strongly on pose alterations, such that a specific weighting of the functions is not necessary.

In a specific example, this means that at least one of the directions of the pose of the objects or markers may be mainly determined with the help of one of the two camera (-systems), while the contribution of the respective other camera is comparatively low.

In a further specific example, the spatial position of the object is tracked exclusively on the basis of the adjusted first position data, particularly at least for a time period for which second position data is not received from the detection system. This could be the case when the line of sight between the detection system and the respective marker is interrupted. In such case the spatial tracking may continue based solely on the microscope camera(-system).

In a second aspect, the invention is directed to a computer program comprising instructions which, when the program is executed by at least one computer, causes the at least one computer to carry out method according to the first aspect. The invention may alternatively or additionally relate to a physical carrier carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:
a) the at least one computer according to the fourth aspect;
b) at least one electronic data storage device storing at least the transformation data; and
c) a surgical microscope for observing a medical procedure carried out on the patient,
wherein the at least one computer is operably coupled to
the at least one electronic data storage device for acquiring, from the at least one data storage device, at least the transformation data, and
the medical device for issuing a control signal to the surgical microscope for controlling the operation of the surgical microscope on the basis of the calibration data.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the invention does not involve or in particular comprise or encompass an invasive step which would represent a substantial physical interference with the body requiring professional medical expertise to be carried out and entailing a substantial health risk even when carried out with the required professional care and expertise.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium which represents the program, for example the aforementioned program, which for example comprises code means which are adapted to perform any or all of the method steps described herein. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
- a computer for processing the absolute point data and the relative point data;
- a detection device for detecting the position of the main and auxiliary points in order to generate the absolute point data and to supply the absolute point data to the computer;
- a data interface for receiving the relative point data and for supplying the relative point data to the computer; and
- a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
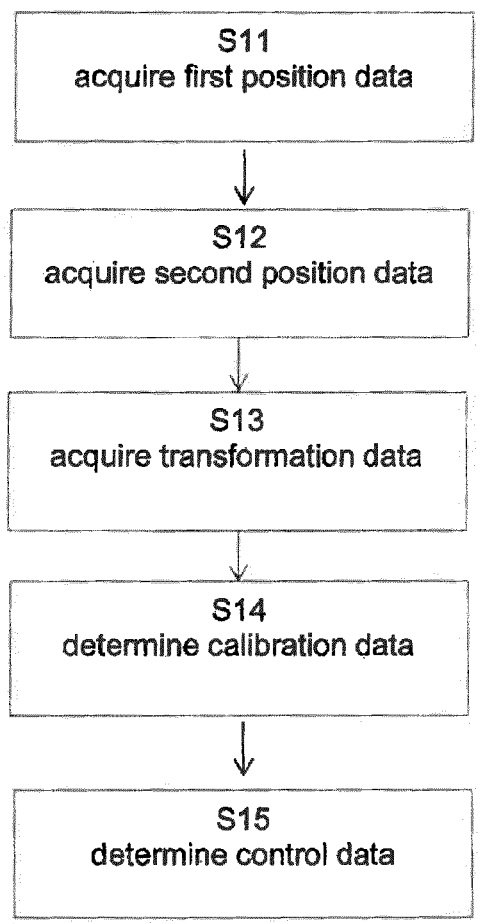
FIG. 1 illustrates the basic steps of a method according to the first aspect.

FIG. 1 shows the basic steps of the method according to the first aspect, in which step S11 encompasses acquiring first position data, step S12 encompasses acquiring second position data, step S13 encompasses acquiring transformation data, step S14 encompasses determining calibration data and step S15 encompasses determining adjusted first position data. At least steps S11, S12 and S13 can be performed in any desired order that differs from the order shown in FIG. 1.

Figure 2:
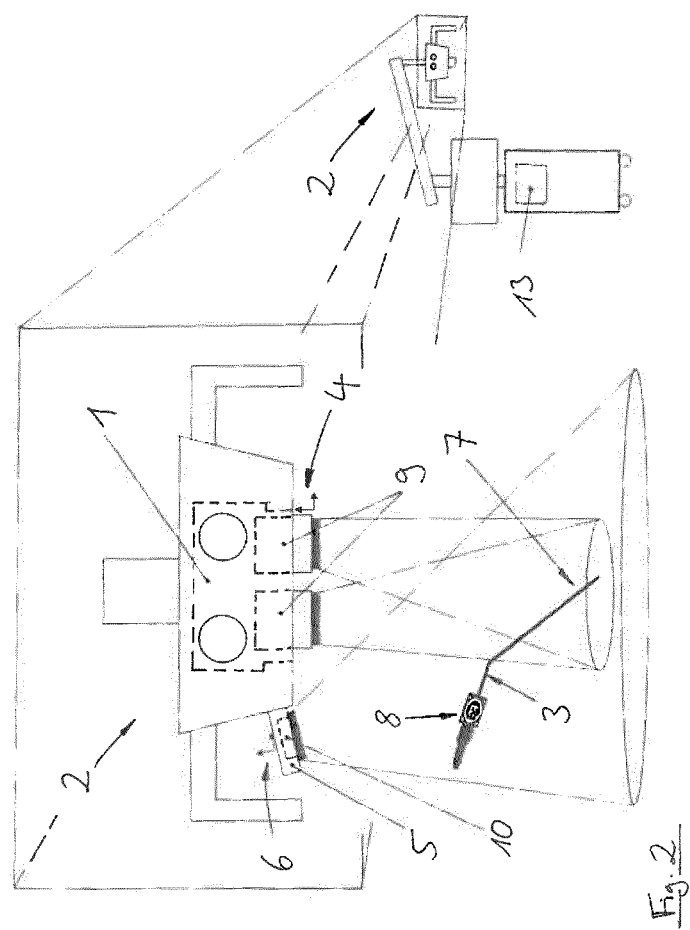
FIG. 2 shows a surgical microscope used in connection with the method according to the first aspect.

FIG. 2 shows a surgical microscope 2 which may be used in connection with the present invention.

The surgical microscope 2 is carried by a movable trolley (not indicated in FIG. 2) which may comprise a computer 13 having at least one processor for performing the method steps outlined in FIG. 1.

The surgical microscope 2 further includes an optical system 1 for guiding an optical path of a received image to a stereoscopic camera 9 as well as to the microscope's eyepieces (not indicated in FIG. 2). A detection system 5 having a monoscopic camera 10 is rigidly attached to the housing of the surgical microscope 2 and to the optical system 1 thereof. Thus, the relative position between the co-ordinate system 4 assigned to the optical system 1 and the co-ordinate system 6 assigned to the detection system 5 remains invariant. Thus, a transformation matrix between the co-ordinate systems 4 and 6 remains invariant, as well.

In the situation shown in FIG. 2, the distal portion 7 of the instrument 3 is located within the field of view of the microscope cameras 9 such that the spatial position thereof can be determined within co-ordinate system 4 based on data derived from the images received by the microscope cameras 9. In a similar manner, the spatial position of the proximal portion 8 can be determined within co-ordinate system 6 based on the image data received by camera 10. Due to the known and predefined spatial arrangement of co-ordinate systems 4 and 6 with respect to each other, the spatial position of sections 7 and 8 can also be transformed to the respective other co-ordinate system 4, 6. Further, the known and predefined spatial arrangement of the instrument portions 7 and 8 relative to each other allows a comparison of the spatial positions of the instrument 3 as detected by the detection system 5 and the microscope 2 respectively.

In case the focus and/or zoom of the microscope cameras 9 is altered, for example upon request of a surgeon operating the microscope 2, a correct calibration of the microscope cameras 9 can be verified by comparing the spatial position of the object as indicated by the 2D-marker at the distal portion which is detected by camera 10, with the spatial position of the instrument 3 as indicated by the ring markers at the distal portion 7 which are detected by cameras 9. In case an undesired deviation in the object's position is determined, a re-calibration of the microscope cameras 9 can be initiated, such that the object's spatial position acquired via the microscope 2 aligns with the object's spatial position acquired via the detection system 5.

After the microscope cameras 9 have been re-calibrated, the object's spatial position can be accurately tracked via the microscope cameras 9 having a new focus-setting and/or zoom-setting.

Figure 3:
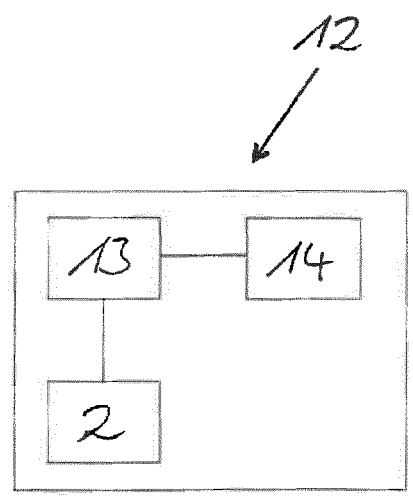
FIG. 3 is a schematic illustration of the system according to the fifth aspect.

FIG. 3 is a schematic illustration of the medical system 1 according to the fifth aspect. The system is in its entirety identified by reference sign 1 and comprises a computer 2, an electronic data storage device (such as a hard disc) 3 for storing at least the patient data and a medical device 4 (such as a radiation treatment apparatus). The components of the medical system 1 have the functionalities and properties explained above with regard to the fifth aspect of this disclosure.

The invention claimed is:

1. A computer-implemented method of calibrating an optical system of a surgical microscope, the method comprising:
    acquiring first position data via the optical system having a first calibration, wherein the first position data describes an estimated spatial position of a distal section of an associated object within a first co-ordinate system assigned to the optical system;
    acquiring second position data via a detection system separate from the optical system, wherein the second position data describes a spatial position of a proximal section of the associated object within a second co-ordinate system assigned to the detection system;
    acquiring transformation data that describes a co-ordinate transformation between the first co-ordinate system and the second co-ordinate system;
    acquiring object model data that describes a predefined relative position between the distal section of the associated object and the proximal section of the associated object;
    determining calibration data based on the first position data, the second position data, the transformation data, and the object model data, wherein the calibration data describes a second calibration of the optical system for which the spatial position of the associated object acquired via the optical system using the second calibration would align with the spatial position of the associated object acquired via the detection system; and
    acquiring adjusted first position data via the optical system using the second calibration, wherein the adjusted first position data describes a corrected spatial position of the associated object within the first co-ordinate system assigned to the optical system.

2. The method according to claim 1, wherein:
    the first calibration and/or the second calibration of the optical system comprises at least one of:
        an intrinsic calibration of a camera of the surgical microscope; and/or
        an extrinsic calibration of the camera of the surgical microscope with respect to a camera of the detection system;
    and/or
    the second calibration partially reflects the first calibration.

3. The method according to claim 1, wherein the acquiring the first position data comprises determining the first position data from one or more images received from a camera integrated with the surgical microscope.

4. The method according to claim 1, wherein the acquiring the first position data comprises acquiring the first position data using a camera of the surgical microscope having one or more of a variable zoom-setting and/or a variable focus-setting.

5. The method according to claim 1, wherein the acquiring the second position data comprises determining the second position data from one or more images received from a camera of the detection system, being separate from a camera of the surgical microscope, wherein the camera of the detection system is rigidly coupled with the surgical microscope and/or comprises a component separate from the surgical microscope.

6. The method according to claim 5, wherein:
    the camera of the detection system has a larger field of view than the camera of the surgical microscope; and/or
    the camera of the detection system has a visual axis that is angled with respect to a visual axis of the camera of the surgical microscope.

7. The method according to claim 6, wherein the camera of the detection system comprises a predefined zoom-setting and/or a predefined focus-setting.

8. The method according to claim 1, further comprising acquiring the first, second and transformation data, determining the calibration data, and acquiring the adjusted first position data:
    upon user request;
    before the surgical microscope is operated;
    in predefined time intervals during the operation of the surgical microscope;
    after a setting of the surgical microscope has been changed, after a viewing direction of the surgical microscope and/or a viewing distance of the surgical microscope has changed; and/or
    after a setup of a zoom-setting of the optical system and/or a focus-setting of the optical system has changed.

9. The method according to claim 1, further comprising:
    determining deviation data based on the first position data, the second position data and the transformation data, the deviation data describing a spatial deviation between the spatial position of the associated object acquired via the optical system and the spatial position of the associated object acquired via the detection system, wherein the determining the calibration data comprises selectively determining the calibration data based on the spatial deviation exceeding a predefined threshold.

10. The method according to claim 1, further comprising simultaneously tracking the spatial position of the associated object based on the adjusted first position data and the second position data, wherein the spatial position within at least one degree of freedom is determined based on a weighted combination of the adjusted first position data and the second position data.

11. The method according to claim 1, further comprising tracking the spatial position of the associated object exclusively based on the adjusted first position data, at least for a time period for which the second position data is not received from the detection system.

12. A non-transitory computer-readable medium storing a computer program comprising instructions that, when executed by a processor of an associated computer, cause the associated computer to carry out a method comprising:
    acquiring first position data via an optical system having a first calibration, wherein the first position data describes an estimated spatial position of a distal section of an associated object within a first co-ordinate system assigned to the optical system;
    acquiring second position data via a detection system separate from the optical system, wherein the second position data describes a spatial position of a proximal section of the associated object within a second co-ordinate system assigned to the detection system;
    acquiring transformation data that describes a co-ordinate transformation between the first co-ordinate system and the second co-ordinate system;

acquiring object model data that describes a predefined relative position between the distal section of the associated object and the proximal section of the associated object;

determining calibration data based on the first position data, the second position data, the transformation data, and the object model data, wherein the calibration data describes a second calibration of the optical system for which the spatial position of the associated object acquired via the optical system using the second calibration would align with the spatial position of the associated object acquired via the detection system; and acquiring adjusted first position data via the optical system using the second calibration, wherein the adjusted first position data describes a corrected spatial position of the associated object within the first co-ordinate system assigned to the optical system.

13. The non-transitory computer-readable medium according to claim 12, wherein the computer program comprising the instructions, when executed by the processor of the associated computer, causes the associated computer to acquire the first position data by:
determining the first position data from one or more images received from a camera integrated with a surgical microscope, or
acquiring the first position data using a camera of the surgical microscope having one or more of a variable zoom-setting and/or a variable focus-setting.

14. The non-transitory computer-readable medium according to claim 12, wherein the computer program comprising the instructions, when executed by the processor of the associated computer, causes the associated computer to acquire the second position data by:
determining the second position data from one or more images received from a camera of the detection system, being separate from a camera of a surgical microscope, wherein the camera of the detection system is rigidly coupled with the surgical microscope and/or comprises a component separate from the surgical microscope.

15. The non-transitory computer-readable medium according to claim 12, wherein the computer program comprising the instructions, when executed by the processor of the associated computer, further causes the associated computer to:
determine deviation data based on the first position data, the second position data and the transformation data, wherein the deviation data describes a spatial deviation between the spatial position of the associated object acquired via the optical system and the spatial position of the associated object acquired via the detection system, wherein the determined calibration data comprises calibration data selectively determined based on the spatial deviation exceeding a predefined threshold.

16. The non-transitory computer-readable medium according to claim 12, wherein the computer program comprising the instructions, when executed by the processor of the associated computer, further causes the associated computer to:
simultaneously track the spatial position of the associated object based on the adjusted first position data and the second position data, wherein the spatial position within at least one degree of freedom is determined based on a weighted combination of the adjusted first position data and the second position data.

17. A medical system, comprising:
at least one computer;
at least one electronic data storage device storing transformation data and instructions; and
a surgical microscope arranged to observe a medical procedure carried out on an associated patient,
wherein the at least one computer is operably coupled with the at least one electronic data storage device for acquiring, from the at least one electronic data storage device, the transformation data and the instructions,
wherein the at least one computer is operable to execute the instructions to calibrate an optical system of the surgical microscope by:
acquiring first position data via the optical system having a first calibration, wherein the first position data describes an estimated spatial position of a distal section of an associated object within a first co-ordinate system assigned to the optical system;
acquiring second position data via a detection system separate from the optical system, wherein the second position data describes a spatial position of a proximal section of the associated object within a second co-ordinate system assigned to the detection system:
acquiring transformation data that describes a co-ordinate transformation between the first co-ordinate system and the second co-ordinate system;
acquiring object model data that describes a predefined relative position between the distal section of the associated object and the proximal section of the associated object;
determining calibration data based on the first position data, the second position data, the transformation data and the object model data, wherein the calibration data describes a second calibration of the optical system for which the spatial position of the associated object acquired via the optical system using the second calibration would align with the spatial position of the associated object acquired via the detection system; and
acquiring adjusted first position data via the optical system using the second calibration, wherein the adjusted first position data describes a corrected spatial position of the associated object within the first co-ordinate system assigned to the optical system,
wherein the at least one computer is operably coupled with the surgical microscope for issuing a control signal to the surgical microscope for controlling the operation of the surgical microscope based on the calibration data that describes the second calibration of the optical system.

18. The medical system according to claim 17, wherein:
the first calibration and/or the second calibration of the optical system comprises at least one of: an intrinsic calibration of a camera of the surgical microscope; and/or an extrinsic calibration of the camera of the surgical microscope with respect to a camera of the detection system; and/or
the second calibration partially reflects the first calibration.

19. The medical system according to claim 17, wherein:
the at least one computer is operable to execute the instructions to acquire the second position data via the detection system separate from the optical system by:
determining the second position data from one or more images received from a camera of the detection system, being separate from a camera of the surgical microscope, wherein the camera of the detection system is rigidly coupled with the surgical microscope and/or comprises a component separate from the surgical microscope.

20. The medical system according to claim 19, wherein:
the camera of the detection system has a larger field of view than the camera of the surgical microscope; and/or
the camera of the detection system has a visual axis that is angled with respect to a visual axis of the camera of the surgical microscope.

* * * * *